United States Patent [19]

Heine et al.

[11] Patent Number: 4,963,014
[45] Date of Patent: Oct. 16, 1990

[54] OPHTHALMOSCOPE

[75] Inventors: Helmut A. Heine, Herrsching; Helmut Rosenbusch, Weilheim; Otto H. Schmidt, Herrsching, all of Fed. Rep. of Germany

[73] Assignee: Propper Manufacturing Co., Ltd., Long Island City, N.Y.

[21] Appl. No.: 492,432

[22] Filed: Mar. 6, 1990

Related U.S. Application Data

[63] Continuation of Ser. No. 171,985, Mar. 23, 1988, abandoned.

[30] Foreign Application Priority Data

Mar. 27, 1987 [DE] Fed. Rep. of Germany ... 8704606[U]

[51] Int. Cl.⁵ .............................................. A61B 3/10
[52] U.S. Cl. .................................................... 351/205
[58] Field of Search ...................... 351/205, 221, 214; 350/432

[56] References Cited

U.S. PATENT DOCUMENTS 4,469,413 10/1988 Shrayangi ........................... 351/205

OTHER PUBLICATIONS

Volk et al., Clinical Ophthalmology, Chapters 32, 50, 51 and 63 1987.
Duke-Elder, Text-Book of Ophthalmology, 1944.

Primary Examiner—Paul M. Dzierzynski
Attorney, Agent, or Firm—Amster, Rothstein & Ebenstein

[57] ABSTRACT

An opthalmoscope comprises a beam of light projecting along an illumination beam path into the eye of a patient and onto the fundus oculi of the eye, and a condenser system arranged in the illumination beam path. The condenser system includes an element having a non-spherical optically effective surface.

7 Claims, 3 Drawing Sheets

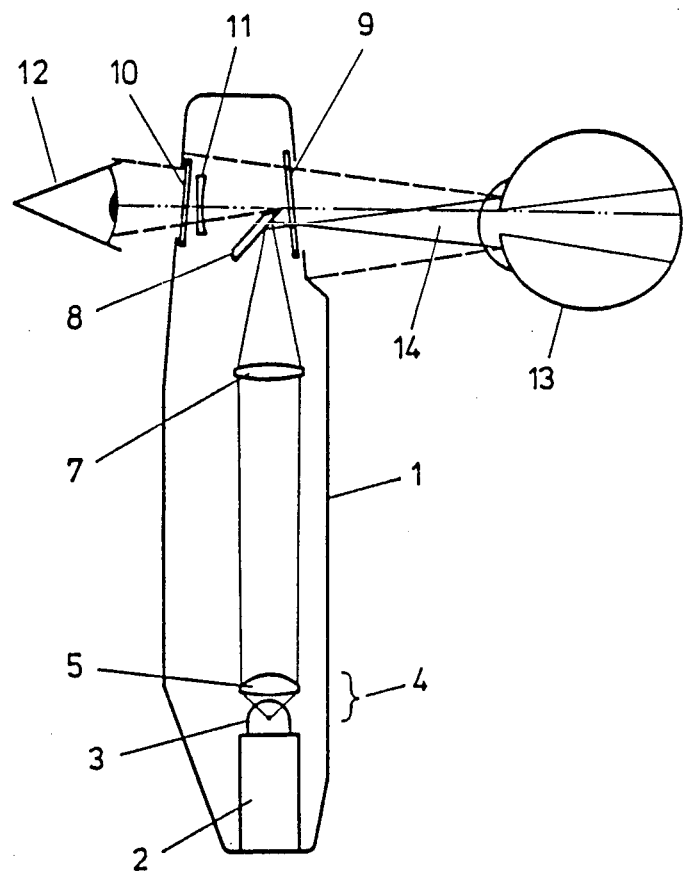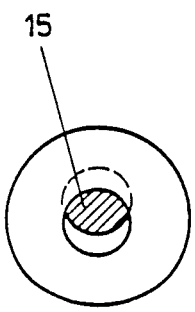
Fig. 1a
Fig. 1b

OPHTHALMOSCOPE

This is a continuation of co-pending application Ser. No. 171,985, now abandoned filed on Mar. 23, 1988.

The invention relates to a direct ophthalmoscope.

The state of the art and the invention are illustrated by means of the drawings.

FIG. 1a is a longitudinal section through a known direct opthalmoscope.

FIG. 1b is a representation of the fundus oculi as seen by an observer with the use of the opthalmoscope of FIG. 1a.

FIG. 2a is the longitudinal section of a second known opthalmoscope.

FIG. 2b is a representation of the fundus oculi as seen by an observer with the use of the opthalmoscope of FIG. 2a.

FIG. 3a is the longitudinal section of a direct opthalmoscope in accordance with the invention.

FIG. 3b is a representation of the fundus oculi as seen by an observer with the use of the opthalmoscope of FIG. 3a.

Figures 2A, 2B:
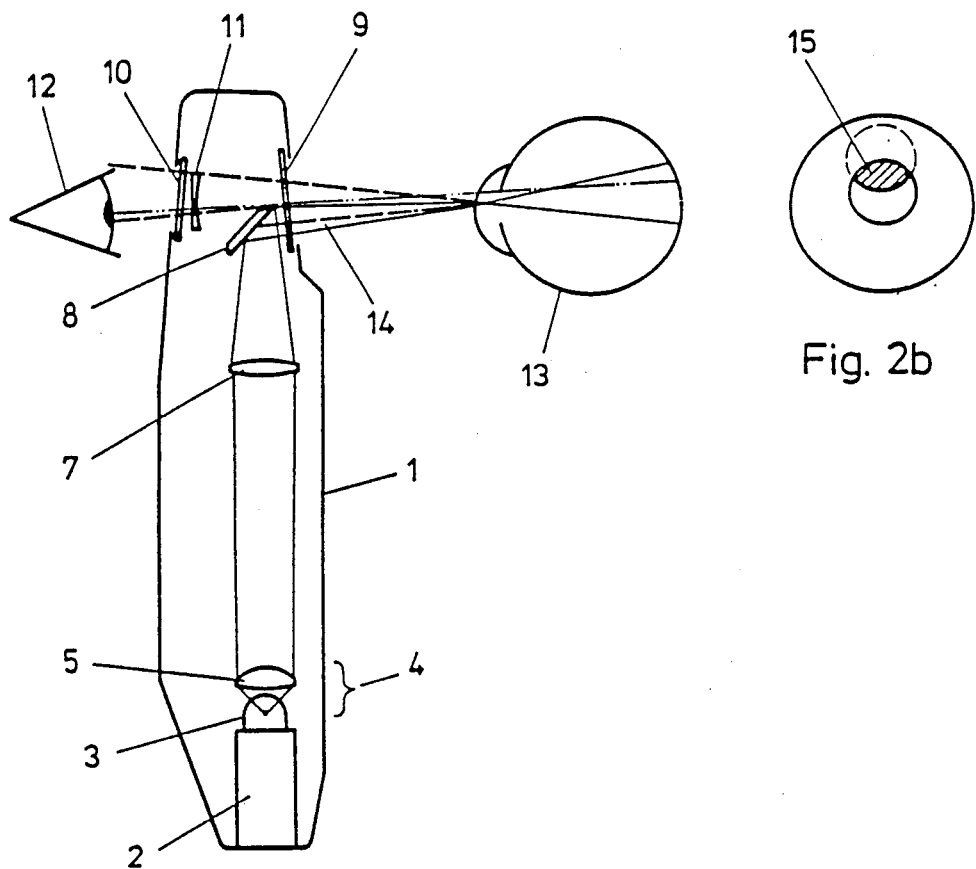

Lamp holder 2, into which electric bulb 3 is introduced, is located in housing of the direct opthalmoscope indicated in FIGS. 1a and 2a. Condenser or condenser system 4, consisting of lens 5 or several lens elements, is located in front of bulb 3. Objective lens 7 and deflection mirror 8, which direct light to the outside through outlet window 9, are located in the illumination beam path behind condenser 4. Another window and lens 11 are arranged at the side of housing opposite outlet window 9. The eye 12 of an observer can observe eye 13 of the patient through window 10 and lens 11 by way of the upper edge of deflection mirror 8 through the outlet window.

In the case of a widely dilated pupil on patient eye 13, a sufficiently large extent of the retina is illuminated by illumination beam 14. If the pupil of patient eye 13 is small, however, only a small part of the light reaches the retina of the patient, especially if the focal point of the lens system is located in the vicinity of deflection mirror 8, as shown in FIG 1a. If illumination beam 14 is focused in the vicinity of the pupil of patient eye 13, on the other hand, only a very narrow somewhat oval area 15 is visible as illuminated for eye 12 of the observer in case of a small patient pupil because of the thereby necessary larger parallax angle, which moreover is displaced upward, unlike the illuminated area 15 as per FIG. 1b into a range lying far outside the middle. If the opthalmoscope of FIG. 1a is used, on the other hand, not only is the illumination intensity low at the fundus oculi, but light falling on patient eye 13 is reflected backward by the iris and cornea in a broad beam to eye 12 of the observer, as indicated in the figures by the areas bounded by dashed lines. This makes the examination difficult if not impossible.

The object of the invention is that of designing an opthalmoscope in which as large an area 15 of the fundus oculi is illuminated with as good a utilization of the available light as possible, whereby reflections at patient eye 13 are avoided or suppressed as much as possible.

This task is achieved according to the invention when the condenser contains at least one lens element which presents at least one optically effective, preferably nonspherical, surface.

Figures 3A, 3B:
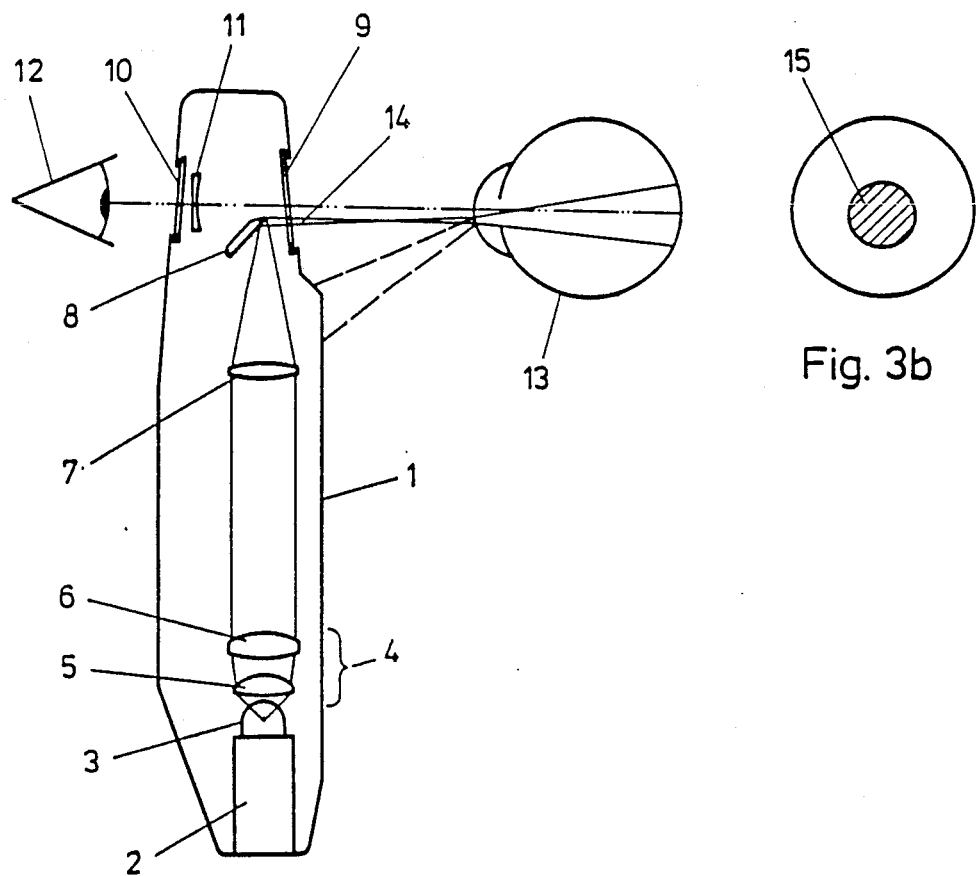

FIG. 3a shows an opthalmoscope designed in this way, in which condenser 4 presents lens 6 with a nonspherical surface in addition to one or more spherical lenses 5.

With the use of such a lens 6 in condenser 4, an approximately tubular course of illumination beam path 14 can be obtained between deflection mirror 8 and patient eye 13, which is very narrow in at least one direction over a relatively broad range. Consequently, the parallax angle between the illumination and observation beam paths can be kept very small, so that an almost circular illuminated area 15 is visible for eye 12 of the observer at the fundus oculi of patient 13. The light from the illumination beam path is thereby well utilized, so that area 15 is not only sufficiently large, but it is also illuminated with strong intensity. Light reflected at the cornea and iris of patient eye 13 is not reflected to eye 12 of the observer but instead to the side and below.

We claim:

1. Direct opthalmoscope apparatus for direct examination of a patient's eye comprising means for originating and projecting a beam of light along an illumination beam path into the eye of a patient and onto the fundus oculi of the eye, said means including a condenser system arranged in the illumination beam path to concentrate light from a light source and an objective system also arranged in the illumination beam path to direct the concentrated light into the patient's eye, said condenser system having at least one element with a nonspherical optically effective surface which is cylindrical to shape the beam of light along the illumination beam path projecting into the eye of a patient.

2. Apparatus in accordance with claim 1 wherein said condenser system further includes a spherical element.

3. Apparatus in accordance with claim 1 wherein said nonspherical optically effective surface shapes the cross-section of the illumination beam.

4. Apparatus in accordance with claim 1 wherein the beam of light projecting into the eye of a patient is tubular in shape.

5. Apparatus in accordance with claim 1 wherein the beam of light projecting into the eye of a patient is narrow in at least one direction over a relatively broad range.

6. Apparatus in accordance with claim 1 wherein the parallel angle between the beam of light path and the observation beam path is small.

7. Apparatus in accordance with claim 1 additionally including means defining an observation beam path from the eye of a doctor into the eye of the patient, said nonspherical optically effective surface shaping the cross-section of the illumination beam path to narrow the same in at least one direction over a relatively broad range, relative to an unshaded illumination beam path, and thereby diminish the parallel angle between the illumination beam path and the observation beam path.

* * * * *